United States Patent
Shah et al.

(10) Patent No.: US 7,875,730 B2
(45) Date of Patent: Jan. 25, 2011

(54) PROCESS FOR MANUFACTURE OF RACEMIC CARVEDILOL

(75) Inventors: Dhiraj R. Shah, Gujarat (IN); Ashish P. Naik, Gujarat (IN); Parva Y. Purohit, Gujarat (IN); Rajivkumar Sharma, Gujarat (IN); Virendra K. Agarwal, Gujarat (IN)

(73) Assignee: Cadila Healthcare Ltd., Gujarat (IN)

( * ) Notice: Subject to any disclaimer, the term of this patent is extended or adjusted under 35 U.S.C. 154(b) by 739 days.

(21) Appl. No.: 10/589,998

(22) PCT Filed: Feb. 22, 2005

(86) PCT No.: PCT/IN2005/000056

§ 371 (c)(1),
(2), (4) Date: Nov. 16, 2007

(87) PCT Pub. No.: WO2005/080329

PCT Pub. Date: Sep. 1, 2005

(65) Prior Publication Data

US 2008/0214833 A1  Sep. 4, 2008

(30) Foreign Application Priority Data

Feb. 23, 2004  (IN) .................. 219/MUM/2004

(51) Int. Cl.
*C07D 209/88* (2006.01)
(52) U.S. Cl. ..................................... 548/444
(58) Field of Classification Search .................. None
See application file for complete search history.

(56) References Cited

U.S. PATENT DOCUMENTS

| | | | |
|---|---|---|---|
| 3,976,779 A | 8/1976 | Leinert et al. | |
| 4,767,784 A | 8/1988 | Zölss et al. | |
| 4,849,530 A | 7/1989 | Zöl et al. | |
| 4,990,668 A | 2/1991 | Mai et al. | |
| 5,071,868 A | 12/1991 | Leinert | |
| 6,140,352 A | 10/2000 | Crowell et al. | |
| 6,699,997 B2 * | 3/2004 | Hildesheim et al. | 548/444 |
| 6,939,986 B2 | 9/2005 | Karpf et al. | |
| 2002/0143045 A1 | 10/2002 | Hildesheim et al. | |

FOREIGN PATENT DOCUMENTS

| | | |
|---|---|---|
| WO | 02/00216 A | 1/2002 |
| WO | 2004/094378 A | 11/2004 |

OTHER PUBLICATIONS

Wei-Min, et al., "Synthesis and Crystal Structure of Carvedilol", Chinese J. Struct. Chem., Sep. 1998, vol. 17, No. 5, pp. 325-328.
Chen, W.-M., et al., "Synthesis and Crystal Structure of Carvedilol" *Chinese Journal of Structural Chemistry*, vol. 17, No. 5 Sep. 1998, pp. 325-328.

* cited by examiner

*Primary Examiner*—Kamal A Saeed
(74) *Attorney, Agent, or Firm*—Ladas & Parry LLP

(57) ABSTRACT

The invention relates to a novel process for the manufacture of Carvedilol of high HPLC purity (>99.5%) having individual impurity less than 0.1%. The product is isolated from reaction mass as a salt with suitable organic acids which on further purification is converted into the free base i.e., Carvedilol.

19 Claims, No Drawings

PROCESS FOR MANUFACTURE OF RACEMIC CARVEDILOL

FIELD OF INVENTION

The present invention relates to an economically viable process for manufacture of racemic Carvedilol. The product is isolated by salt formation with suitable organic acid. The salt is purified and treated with a base to provide Carvedilol with high HPLC purity (>99.5%) having individual impurity less than 0.1%.

BACKGROUND OF THE INVENTION

Carvedilol, chemically known as (±) 1-(9H-carbazol-4-yloxy))-3-[2-(2-methoxyphenoxy)ethyl]amino-2-propanol, (CAS Registry No. [72956-09-3]), having following structural formula (I)

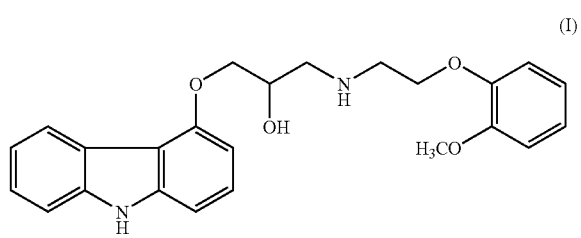

(I)

Carvedilol having structural formula (I) is a nonselective β-adrenergic blocking agent with $\alpha_1$ blocking activity.

Carvedilol has an asymmetric carbon and exists either as individual stereoisomers or in racemic form. The nonselective β-adrenergic activity of Carvedilol is present in the S(−) enantiomer and $\alpha_1$ blocking activity is present in both the R(+) and S(−) enantiomers at equal potency. It is marketed in racemic form.

EP 0127099 describes the preparation of both the racemate and stereoisomers. U.S. Pat. No. 4,503,067, U.S. Pat. No. 4,824,963, EP 0127099, EP 918055, EP 1142873, WO 02/00216 patents incorporated herein by reference discloses various processes for preparing Carvedilol.

U.S. Pat. No. 4,503,067 discloses a process for preparation of Carvedilol by the following reaction scheme-I.

(Scheme-I)

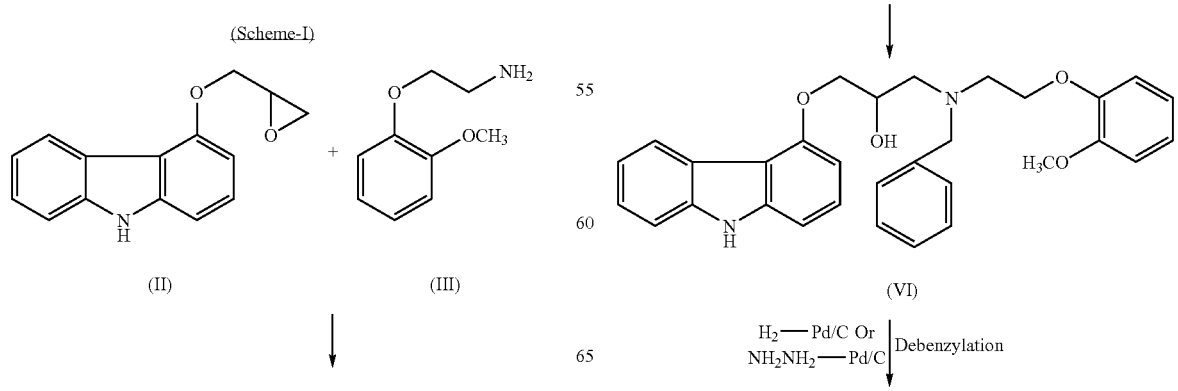

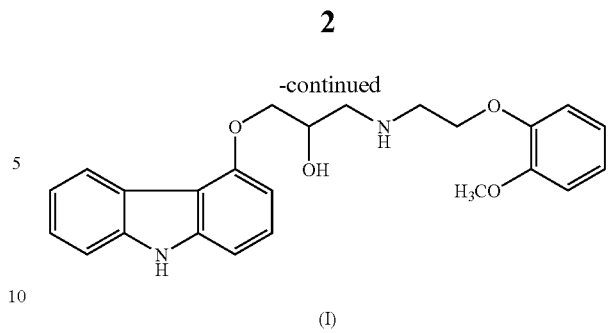

(I)

4-(oxiran-2-ylmethoxy)-9H-carbazole (II) is reacted with 2-(2-methoxyphenoxy)ethylamine (III) in a molar ratio of 1:1.1 and the reaction was carried out at 50° C. temperature for 25 hours. The process gives low yield of 39.42%. A considerable amount of by-product (formula IV) is formed, resulting in a low yield of desired product and making the purification difficult.

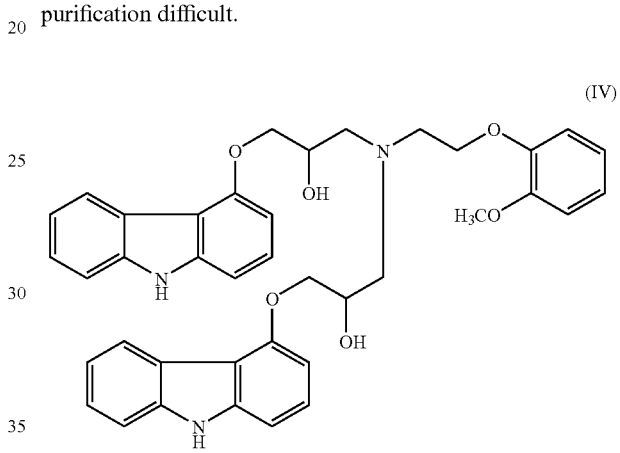

(IV)

EP 918055 A1, EP 1142973 A2 discloses the preparation of Carvedilol as mentioned in scheme-II (Scheme-II)

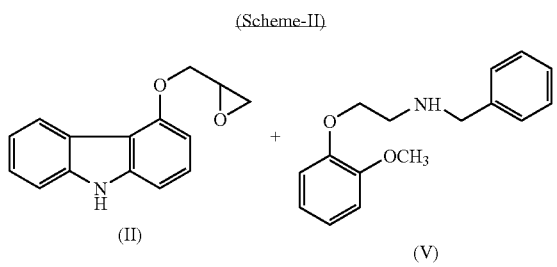

↓

H$_2$—Pd/C Or NH$_2$NH$_2$—Pd/C | Debenzylation

↓

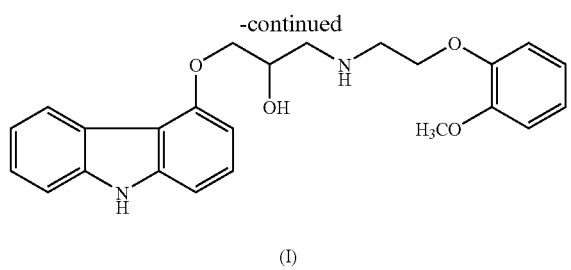

(I)

The process involves the catalytic N-debenzylation at the final stage. According to literature knowledge, N-debenzylation reaction never goes for 100% completion, leading the traces of N-benzyl Carvedilol (VI) as major impurity in final product. The European pharmacopoeia has covered the limit of this impurity (VI) not more than 0.02% due to its toxic nature and practically it is very difficult to achieve this level by the process based on scheme-II.

Recently US 2002/0143045 A1 discloses the preparation of Carvedilol by reaction of 4-(oxiran-2-ylmethoxy)-9H carbazole (II) with 2-(2-methoxyphenoxy)ethylamine (III) in 1:1.5 to 1:100 molar ratio without solvent in neat condition at 100° C. to minimize the formation of compound (IV) as by-product. This patent does not disclose the yield and the purity of the Carvedilol obtained. At higher temperature, in the absence of solvent there is possibility of degradation that results in low yield. Also the use of large amount of 2-(2-methoxyphenoxy)ethylamine (III) makes the process uneconomical.

It is evident from above that though prior art looks conceptually very good, but practically it is very difficult to implement at large scale production. According to the U.S. Pat. No. 4,503,067, the reaction time itself is 25 hours with lesser yields. While in WO 02/00216 the product is crystallized out in 40 hours at 4° C. and according to the European Patent EP 918055, the final stage involves catalytic hydrogenation for debenzylation. Thus these processes are not feasible on production scale.

Objects of the Present Invention

Accordingly, it an important object of the present invention to provide a process for the preparation of pure Carvedilol by an economically viable process.

It is another object of the present invention to provide a process for manufacture of Carvedilol having purity (>99.5%) with individual impurities less than 0.1%, by removing drawbacks of the prior arts.

DETAILED DESCRIPTION

Accordingly the present invention provides a simplified process for the preparation of pure Carvedilol comprising the steps; (i) condensation of compounds (II) and (III) in described molar ratio in presence of preferred solvent, (ii) preparation of the salt of Carvedilol with suitable organic acid in a preferred solvent, (iii) isolation and purification of the salt to get pure Carvedilol from the salt by treatment with a base. Carvedilol thus obtained is purified to get required quality and desired polymorphic form of the product. The embodiment is disclosed in the scheme-III.

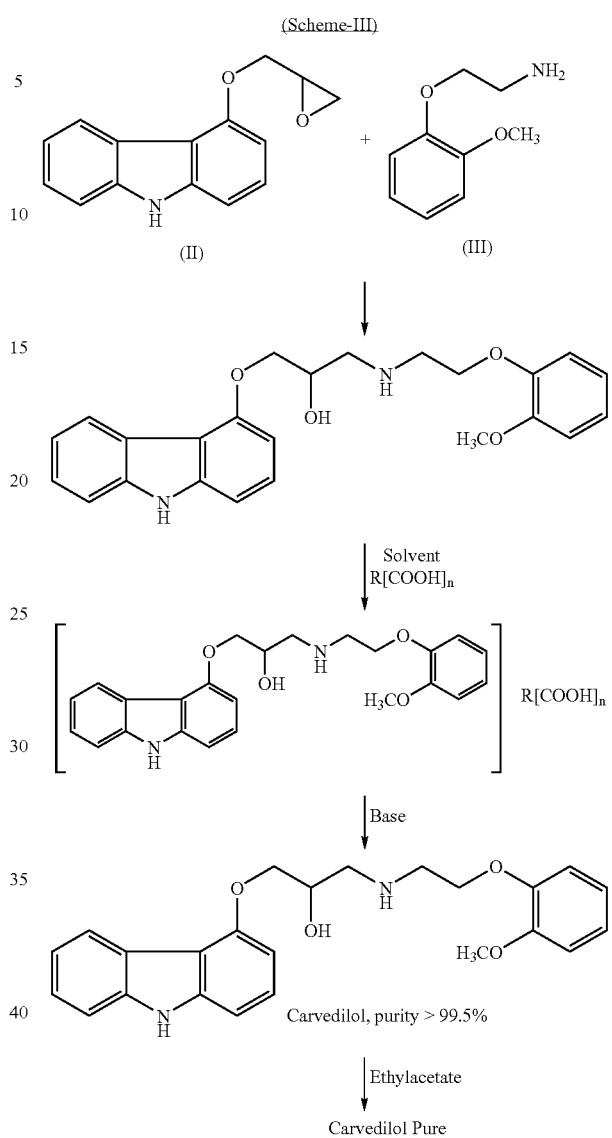

4-(oxiran-2-ylmethoxy)-9H-carbazole (II) is reacted with 2-(2-methoxyphenoxy)ethylamine (III) in a molar ratio of 1:1.15 to 1:1.45, preferably, in a molar ratio of 1:1.4.

This reaction is carried out at a temperature of 30° C. to 90° C., preferably, at 50° C. to 80° C., most preferably, at 70° C. to 80° C. in a suitable solvent such as primary, secondary or tertiary lower alcohol containing 1-6 carbon atoms, esters i.e. $CH_3COOR$, where R=straight or branched chain alkyl group containing 1-4 carbon atoms, nitrile, R—CN where R is where R is straight or branched chain alkyl group containing 1-4 carbon atoms.

The preferred solvent is methanol, ethanol, 2-propanol, isobutanol, tertiary butanol, acetonitrile, and ethyl acetate. Most preferred solvent is 2-propanol.

The reaction is carried out for 10 minutes to 20 hours, preferably, for 40 to 90 minutes, most preferably for 60 minutes.

After completion of reaction, the reaction mass is then added to a solution of carboxylic acid having general formula $R'(COOH)_n$ whereas, n=1 and R'=(un) substituted aryl group i.e. benzoic acid, salicylic acid, etc. and n=2 and R'=(un) substituted alkyl group i.e. oxalic acid, tartaric acid, etc. in a suitable solvent as described above.

Most preferred carboxylic acid is salicylic acid.

During the addition of reaction mixture into the solution of carboxylic acid, the temperature is maintained at 20° C. to 90° C., preferably at 75° C. to 85° C.

The precipitated salt of Carvedilol is isolated by known art i.e., filtration or centrifugation. This salt contains about 1.5-2.5% of compound IV as a major impurity.

The salt is purified by crystallization from an organic solvent. Organic solvent is selected from primary, secondary or tertiary aliphatic alcohol containing 1-4 carbon atoms, esters $CH_3COOR$ where R is as mentioned above, preferably ethyl. This crystallization reduced the amount of impurity to about 1-1.5%.

The salt is then treated with suitable organic or inorganic base in water-solvent system to get Carvedilol. Inorganic base is alkali metal carbonate, bicarbonate or hydroxides. Organic base is selected from a straight, branched or cyclic primary, secondary or tertiary aliphatic amine containing 1 to 6 carbon atoms. The most preferred inorganic base is sodium hydroxide while organic base is triethylamine.

Organic solvent is selected from primary, secondary or tertiary aliphatic alcohol containing 1-4 carbon atoms, esters $CH_3COOR$ where R is as mentioned above, preferably ethyl.

Carvedilol is isolated by known arts such as filtration or centrifugation and then purified by crystallization from an organic solvent. Organic solvent includes primary, secondary or tertiary aliphatic alcohol having containing 1-4 carbon atoms, esters such as $CH_3COOR$ where R containing straight or branched chain alkyl group having containing 1-4 carbon atoms. The product is again recrystallized from the same solvent. The most preferred solvent is Ethylacetate.

Advantages of the Present Invention Over the Prior Art

1. Quantity of 2-(2-methoxyphenoxy)ethylamine is reduced.
2. The reaction is conducted in a solvent at a reflux temperature. This reduces reaction time and avoids high temperature e.g. 100° C.
3. The product is isolated as a salt and the salt is purified. This gives product of better quality, all the major impurity goes into the mother liquor.
4. Carvedilol obtained by the disclosed embodiment complies EP pharmaceutical specifications.
5. Organic acid is recovered and recycled.
6. Due to high yield and purity, disclosed embodiment is commercially viable.

The present invention will be more fully understood from the following examples which illustrate. It will be appreciated by persons skilled in the art that various modification of the invention may be possible without departing from the spirit and scope of the invention.

EXAMPLE: 1

Preparation of Carvedilol Salicylate

A mixture of 4-(oxiran-2-ylmethoxy)-9H-carbazole (II) (25.0 g, 104.60 mmole) and 62.5 ml-2-propanol is heated to 70° C. to 80° C. To this 2-(2-methoxyphenoxy)ethylamine (III) (20.96 g, 125.52 mmole) is added in one lot. The temperature of the reaction mass is raised to 80° C. to 85° C. and refluxed for 1.0 hour. The reaction mixture is added into the preheated (80° C. to 85° C.) solution of salicylic acid (18.77 g, 135.98 mmoles) in 187.5 ml 2-propanol. This reaction mass is further refluxed for 2.0 hours, cooled to 50° C. to 55° C. and stirred for one hour at this temperature. The solid is filtered followed by three 33 ml wash with hot (50° C. to 55° C.) 2-propanol. The wet product dried at 60° C. to 65° C. for 6 hours or till constant weight gives 32.5 g (Yield=57%) of Carvedilol salicylate, which contains about 2-2.5% of compound (IV) as an impurity.

HPLC Purity=92.5-95.0%

Melting point.=164° C.-166° C.

EXAMPLE: 2

Preparation of Carvedilol Salicylate:

A mixture of 4-(oxiran-2-ylmethoxy)-9H-carbazole (II) (25.0 g, 104.60 mmole) and 62.5 ml 2-propanol is heated to 70° C. to 80° C. To this 2-(2-methoxyphenoxy)ethylamine (III) (25.33 g, 151.67 mmole) is added in one lot. The temperature of the reaction mass is then raised to 80° C. to 82° C. and refluxed for 1 hour. The reaction mixture is added into the preheated (80° C. to 85° C.) solution of salicylic acid (18.77 g, 135.98 mmoles) in 187.5 ml of 2-propanol. The reaction mass is further refluxed for 2 hours, cooled to 50° C. to 55° C. and stirred for 1 hour at this temperature. The solid is filtered, followed by three 33 ml wash with hot (50° C. to 55° C.) 2-propanol. The wet product dried at 60° C. to 65° C. for 6 hours or till constant weight gives 39.75 g (Yield 70%) of Carvedilol salicylate, which contains about 2-2.5% of compound (IV) as an impurity.

HPLC purity=92.5-95%

Melting point=164° C.-166° C.

EXAMPLE: 3

Process of Purification for Carvedilol Salicylate:

A mixture of Carvedilol salicylate (39.0 g 39.81 mmole) and ethyl acetate (312 ml) is stirred at 70° C. to 75° C. for 30 minutes then cooled to 50° C. to 55° C. and stirred at that temperature for 1 hour. The content is filtered at same temperature and washed with hot (50° C. to 55° C.) ethyl acetate, the product is dried at 60° C. to 65° C. for 6 hours or till constant weight to afford 37.0 g of pure Carvedilol salicylate (Recovery=94.87%), which contains about 1.0-2.0% of compound (IV) as an impurity.

HPLC purity=94-97%

Melting point=165° C.-167° C.

EXAMPLE: 4

Preparation of Carvedilol Benzoate:

A mixture of 4-(oxiran-2-ylmethoxy)-9H-carbazole (II) (25.0 g, 104.60 mmole) and 62.5 ml 2-propanol is heated to 70° C. to 80° C. To this 2-(2-methoxyphenoxy)ethylamine (III) (25.33 g, 151.67 mmole) is added in one lot. The temperature of reaction mass is raised to reflux (80° C. to 85° C.) and maintained at this temperature for 1 hour. After that, this reaction mass was added to the pre-heated (80° C. to 85° C.) solution of benzoic acid (18.5 g) in 2-propanol (287.5 ml) and continued the reflux for next 2-hour, cooled to 50° C. to 55° C. and maintained the same temperature for 1 hr. The product filtered at same temperature followed by three 33.5 ml wash with hot (50° C. to 55° C.) 2-propanol. The wet product dried at 60° C. to 65° C. for 6-8 hours or till constant weight gives 36.5 g of Carvedilol benzoate (Yield=66%).

EXAMPLE: 5

Preparation of Carvedilol Tartarate:

A mixture of 4-(oxiran-2-ylmethoxy)-9H-carbazole (II) (25.0 g, 104.60 mmole) and 62.5 ml 2-propanol is heated to 70° C. to 80° C. To this 2-(2-methoxyphenoxy)ethylamine (III) (25.33 g, 151.67 mmole) is added in one lot. The temperature of reaction mass is raised to reflux (80° C. to 85° C.) and maintained at this temperature for 2 hour. After that, this reaction mass is added to the pre-heated (80° C. to 85° C.) solution of L(+) tartaric acid (24.32 g) (162.1 mmole) in 2-propanol (287.5 ml) and continued the reflux for next 1 hour, cooled to 50° C. to 55° C. and maintained for 1 hour. The product is filtered at the same temperature (50° C. to 55° C.) followed by three 33.5 ml wash with hot (50° C. to 55° C.) 2-Propanol. The wet product dried at 60° C. to 65° C. for 6-8 hours or till constant weight gave 33.0 g of Carvedilol tartarate (Yield 56.89%).

EXAMPLE: 6

Preparation of Carvedilol Oxalate:

A mixture of 4-(oxiran-2-ylmethoxy)-9H-carbazole (II) (25.0 g, 104.60 mmole) and 62.5 ml 2-propanol is heated to 70° C. to 80° C. To this 2-(2-methoxyphenoxy)ethylamine (III) (25.33 g, 151.67 mmole) is added in one lot. The temperature of reaction mass is raised to reflux (80° C. to 85° C.) and maintain at this reaction temperature for one hour. After that, this reaction mass is added to the pre-heated (80° C. to 85° C.) solution of oxalic acid (14.6 g) (162.13 mmole) in 2-propanol (287.5 ml) and continued the reflux for next one-hour, cooled to 50° C. to 55° C. and maintain for 1 hour. The product is filtered at the same temperature followed by three 33.5 ml wash with hot (50° C. to 55° C.) 2-propanol. The wet product dried at 60° C. to 65° C. for 6-8 hours or till constant weight gives 42.0 g of Carvedilol Oxalate (Yield 80.95%).

EXAMPLE: 7 (A)

Preparation of Carvedilol from Carvedilol Salicylate:

A mixture of Carvedilol salicylate (36.0 g, 66.18 mmole) and 2-propanol (108 ml) is heated to 50° C. to 55° C. To this, a solution of sodium hydroxide (4.5 g) in water (36 ml) is added slowly in about 30 minutes. The solution is then stirred at 65° C. to 70° C. for 15 minutes and filtered, followed by two 18 ml wash with hot (55° C. to 60° C.) 2-propanol. The filtrate is cooled to 30° C. to 40° C., 18 ml of water is added and stirred at 25° C. to 35° C. for 3 hours. The precipitated product is filtered, followed by two 30 ml wash with water. The wet product dried at 50° C. to 55° C. till constant weight gives 24.5 g of Carvedilol (Yield=91.21%).

HPLC purity 98.5-99.5%

Impurity (IV) 0.5%-1.0%

EXAMPLE: 7 (B)

Preparation of Carvedilol from Carvedilol Salicylate:

A mixture of Carvedilol salicylate (25.0 g, 45.95 mmole) and ethyl acetate (250 ml) are cooled to 10° C. to 15° C. To this solution triethylamine (10.16 g, 100.63 mmole) is added within 30 minutes. Slowly temperature is raised to 25° C. to 35° C. and maintained at the same temperature for next 30 minutes followed by addition of sodium chloride solution (50 g sodium chloride+250 ml water) and stirred for 30 minutes. Layers separated and ethyl acetate layer is washed with solution of sodium chloride (50 g) and sodium carbonate (100 g) prepared in 250 ml water. The ethyl acetate layer is charcoalised with 2.5 g activated carbon followed by filtration through hyflosupercell. The hyflosupercell bed is washed with two 25 ml ethyl acetate. All ethyl acetate layers are combined and concentrated by removal of ethyl acetate ca. 45% at 75° C. to 80° C. The resulting solution is slowly cooled 25° C. to 40° C. and maintained for 3 hours at this temperature. The product is filtered, followed by two 12.5 ml wash with ethyl acetate and the wet cake dried at 50° C. to 55° C. till constant weight gives 17.0 g of Carvedilol (Recovery=68%).

HPLC Purity=98.5-99.5%

Impurity Compound (IV)=0.5-1.0%

Melting point=113° C.-116° C.

EXAMPLE: 8

Purification of Carvedilol:

Carvedilol (24.0 g) (obtained from experiment-7) is heated with ethyl acetate (192 ml) at 60° C. to 62° C. to get a clear solution. To this, activated carbon (2.4 g) is added and stirred at 70° C. to 75° C. for 1 hour. It is filtered through hyflosupercell followed by two 22 ml wash with hot (60° C. to 65° C.) ethyl acetate. The filtrate and washings were combined and 108 ml ethyl acetate is distilled out at atmospheric pressure. The resulting solution is slowly cooled to 25° C. to 30° C. and stirred for 2 hours. The product is filtered and washed with two 12 ml ethyl acetate. The product dried at 50° C. to 55° C. till constant weight gives 19.5 g of Carvedilol (Recovery=81.25%).

HPLC Purity=>99.5%

Impurity compound (IV)=<0.15%

Melting point=113° C.-115° C.

EXAMPLE-9

Preparation of Carvedilol Form-II:

Carvedilol (19.0 g) (obtained from experiment-8) is heated with ethyl acetate (152 ml) at 60° C. to 65° C. to get clear solution. To this activated carbon (1.9 g) is added and stirred at 70° C. to 75° C. for 1 hour. It is filtered through hyflosupercell followed by two 9.5 ml wash of hot ethyl acetate (60° C. to 65° C.). The filtrate and the washings are combined and 86 ml ethyl acetate is distilled out at atmospheric pressure. The resulting solution is slowly cooled to 25° C. to 30° C. and stirred for 2 hours. The product is filtered and washed with two 9.5 ml ethyl acetate. The product dried at 50° C. to 55° C. till constant weight gives 17.0 g of Carvedilol Form-II (Recovery=89.5%)

HPLC purity=>99.5

All individual impurities=<0.10%

Melting point=113° C.-116° C.

Note: By similar fashion, the other salts e.g. benzoate, oxalate and tartarate of Carvedilol were converted into Carvedilol of high HPLC purity.

We claim:

1. A process for the manufacture of Carvedilol comprising the steps of :
   a) reacting 4-(oxiran-2-ylmethoxy)-9H-carbazole (epoxide) (compound of formula-II)

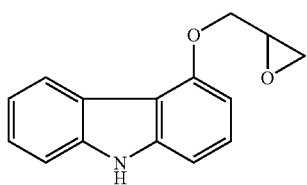

with 2-(2-methoxyphenoxy) ethylamine (compound of formula-III)

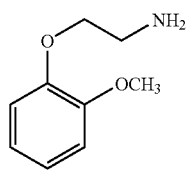

at a ratio of 1:1.15 to 1:1.45, at temperature 30° C. to 90° C. in a suitable organic solvent;

b) preparing the salt of Carvedilol with suitable organic acid in a solvent;
c) isolating the product as a salt with organic acid from an organic solvent;
d) purifying the salt from organic solvent;
e) treating said salt with a base to get free Carvedilol; and,
f) purifying Carvedilol from organic solvent.

2. A process as claimed in claim 1, wherein the compound of formula-II and compound of formula-III are reacted at a molar ratio from 1:1.4.

3. A process as claimed in claim 1, wherein the reaction step (a) is carried out at 50° C. to 85° C.

4. A process as claimed in claim 1, wherein in step (a), said solvent is selected from aliphatic alcohols containing branched or straight chain 1-4 carbon atoms; aliphatic nitriles branched or straight chain containing 1 to 4 carbon atoms and a compound of the formula $CH_3COOR$ where R containing alkyl group having branched or straight chain 1 to 4 carbon atoms.

5. A process as claimed in claim 4, wherein said solvent is 2-propanol.

6. A process as claimed in claim 1, wherein in step (c) the product is isolated as a salt with organic acid.

7. A process as claimed in claim 6, wherein the acid is selected from salicylic acid, benzoic acid, oxalic acid, or tartaric acid.

8. A process as claimed in claim 1, wherein the purification step is performed in organic solvent.

9. A process as claimed in claim 8, wherein the organic solvent is selected from aliphatic alcohols containing branched or straight chain 1-4 carbon atoms; aliphatic nitriles branched or straight chain containing 1 to 4 carbon atoms and a compound of the formula $CH_3COOR$ where R containing alkyl group having branched or straight chain 1 to 4 carbon atoms.

10. A process as claimed in claim 9, wherein the solvent is ethyl acetate.

11. A process as claimed in claim 1, wherein in step (e), Carvedilol is obtained by reacting salt of Carvedilol with organic or inorganic base in the presence of organic solvent containing water.

12. A process as claimed in claim 11, wherein said inorganic base is selected from alkali metal hydroxides, carbonates or bicarbonates.

13. A process a claimed in claim 11, wherein said organic base is selected from aliphatic straight or branched chain primary, secondary or tertiary amines containing alkyl groups having 1-6 carbon atoms or cyclic amines containing 1-6 Carbon atoms.

14. A process as claimed in claim 11, wherein the base is selected from sodium hydroxide and triethyl amine.

15. A process as claimed in claim 1, wherein in step (e), the organic solvent is selected from a group of lower aliphatic alcohols having straight or branched chain alkyl group with 1-4 carbon atoms.

16. A process as claimed in claim 15, wherein the ratio of 2-propanol:water is 5:5.

17. A process as claimed in claim 15, wherein the alcohol is 2-propanol.

18. A process as claimed in claim 16, wherein the ratio of 2-propanol:water is 4:1.5.

19. A process as claimed in claim 3, wherein the reaction step (a) is carried out at 75° C. to 85° C.

* * * * *